United States Patent
Schostek et al.

(10) Patent No.: US 12,171,580 B2
(45) Date of Patent: Dec. 24, 2024

(54) MEDICAL CAPSULE INCLUDING AN ACTIVATION CIRCUIT

(71) Applicant: Ovesco Endoscopy AG, Tübingen (DE)

(72) Inventors: Sebastian Schostek, Tübingen (DE); Gunnar Anhöck, Tübingen (DE); Marc O. Schurr, Tübingen (DE)

(73) Assignee: Ovesco Endoscopy AG (DE)

(*) Notice: Subject to any disclaimer, the term of this patent is extended or adjusted under 35 U.S.C. 154(b) by 0 days.

(21) Appl. No.: 17/160,937

(22) Filed: Jan. 28, 2021

(65) Prior Publication Data
US 2021/0236062 A1   Aug. 5, 2021

(30) Foreign Application Priority Data
Jan. 31, 2020 (EP) .................................. 20154972

(51) Int. Cl.
*A61B 5/00* (2006.01)
*A61B 50/30* (2016.01)
*A61B 1/00* (2006.01)
*A61B 5/02* (2006.01)
*A61B 5/07* (2006.01)

(52) U.S. Cl.
CPC .......... *A61B 5/6861* (2013.01); *A61B 5/0084* (2013.01); *A61B 5/4255* (2013.01); *A61B 5/7435* (2013.01); *A61B 5/7475* (2013.01); *A61B 50/30* (2016.02); *A61B 1/00032* (2013.01); *A61B 5/02042* (2013.01);
(Continued)

(58) Field of Classification Search
CPC ...... A61B 5/6861; A61B 50/30; A61B 5/0084
See application file for complete search history.

(56) References Cited

U.S. PATENT DOCUMENTS 3,556,083 A * 1/1971 Grichnik .............. A61B 5/0531
                                                                    600/547
5,217,449 A   6/1993 Yuda et al.
(Continued)

FOREIGN PATENT DOCUMENTS

CN   106823113 A   6/2017
EP   0460327 A1   12/1991
(Continued)

OTHER PUBLICATIONS

G. Gunlu, "Dynamically Reconfigurable Independent Cellular Switching Circuits for Managing Battery Modules," in IEEE Transactions on Energy Conversion, vol. 32, No. 1, pp. 194-201, Mar. 2017, doi: 10.1109/TEC.2016.2616190 (Year: 2017).*

(Continued)

*Primary Examiner* — Sean D Mattson
(74) *Attorney, Agent, or Firm* — Buchanan Ingersoll & Rooney PC

(57) ABSTRACT

A medical capsule including an electrical circuit and an internal power source for selectively supplying the electrical circuit with electrical energy, wherein at least a photosensitive element is provided for initiating a supply of electrical energy to the electrical circuit when a light signal having a predetermined intensity is irradiated and the invention related to a system comprising a medical capsule in a package, and an extracorporeal device including a light source for emitting a light beam, wherein the package of the medical capsule is adapted and provided to be permeable for the predetermined intensity.

16 Claims, 4 Drawing Sheets

(52) U.S. Cl.
CPC ....... *A61B 5/073* (2013.01); *A61B 2560/0209* (2013.01); *A61B 2562/0233* (2013.01)

(56) References Cited

U.S. PATENT DOCUMENTS

| | | | | |
|---|---|---|---|---|
| 7,763,009 | B1* | 7/2010 | Weiss | A61B 5/6848 |
| | | | | 604/507 |
| 8,398,543 | B2* | 3/2013 | Takahashi | A61B 1/041 |
| | | | | 324/207.13 |
| 8,454,495 | B2* | 6/2013 | Kawano | A61B 1/041 |
| | | | | 600/103 |
| 2004/0000713 | A1* | 1/2004 | Yamashita | H01L 35/32 |
| | | | | 374/E7.035 |
| 2005/0049488 | A1* | 3/2005 | Homan | A61B 1/041 |
| | | | | 600/407 |
| 2005/0272973 | A1* | 12/2005 | Kawano | A61B 1/00144 |
| | | | | 604/890.1 |
| 2008/0257768 | A1* | 10/2008 | Uchiyama | A61B 1/041 |
| | | | | 600/101 |
| 2009/0192353 | A1* | 7/2009 | Segawa | A61B 5/073 |
| | | | | 600/118 |
| 2010/0324365 | A1 | 12/2010 | Marquez | |
| 2011/0184235 | A1* | 7/2011 | Schostek | A61B 1/00158 |
| | | | | 600/109 |
| 2015/0011829 | A1* | 1/2015 | Wang | A61B 1/045 |
| | | | | 600/118 |
| 2016/0136104 | A1* | 5/2016 | Niichel | A61K 41/0028 |
| | | | | 424/452 |

FOREIGN PATENT DOCUMENTS

| | | |
|---|---|---|
| JP | 2015509402 A | 3/2015 |
| WO | 2013126178 A1 | 8/2013 |

OTHER PUBLICATIONS

Extended European Search Report for European Application No. 201 549 72.2 , dated Jul. 31, 2020, 8 pages.

Office Action (Notice of Reasons for Refusal) issued Oct. 8, 2024, by the Japanese Patent Office in corresponding Japanese Patent Application No. 2021-013422 and an English translation of the Office Action. (8 pages).

* cited by examiner

MEDICAL CAPSULE INCLUDING AN ACTIVATION CIRCUIT

This application claims priority to European Patent Application No. EP 20154972.2, filed Jan. 31, 2020, which is incorporated herein by reference.

TECHNICAL FIELD

The present invention relates to a medical capsule including an electrical circuit and an internal power source for selectively supplying the electrical circuit with electrical energy and to a system comprising a medical capsule in a package and an extracorporeal device including a light source for emitting a light beam.

BACKGROUND OF THE INVENTION

An acute upper gastrointestinal bleeding event is an emergency situation which requires immediate endoscopic assessment and treatment. The patient swallows the medical capsule if gastrointestinal bleeding is suspected. In the medical capsule, an electrical circuit comprising sensors is included and the electrical circuit is provided to detect information about the bleeding status. This information about the bleeding status is displayed by particularly telemetric communication of the capsule with an extracorporeal device/receiver. Therefore, a telemetric real-time intracorporeal bleeding sensor can help in the timely diagnosis of an acute upper gastrointestinal bleeding event.

This invention relates to various medical and clinical use scenarios and procedures, and is not limited to the use scenario described/procedure above.

An active medical device such as a medical capsule to be swallowed contains by definition an energy source, in most cases a battery, and a functional part that mostly consists of electronics including sensors and/or actuators that are designed to serve an intended medical purpose. In particular, devices that are intended to be used within the patients' body, such as swallowable medical capsules or any kind of medical implants, must have an enclosure that protects the internal functional elements including the power source from undesired interactions with the human body. For example, the contact material to the body must be biocompatible in order to prevent any undesired reactions of the body such as intoxication or inflammation, and the enclosure in turn must be tight in order to prevent body fluids to intrude into the device and interfere with/corrode the components of the integrated functional elements.

These requirements and circumstances in connection with the limited amount of power stored in the internal power source of an active medical device lead to high demands on the activation of the device. While a mechanical switch which operates on the principle of physical contact/non-contact between electrical conductors to be configured by mechanical displacement of parts of the mechanical switch has the advantage that there is no conductivity given when in an OFF-state, it poses high challenges of integrating such a switch in a way that the enclosure of the medical device complies with requirements of integrity and biocompatibility outlined above.

Other, non-mechanical solutions to activate a medical device that can be remotely operated and therefore integrated within an enclosure of a medical device without compromises on its integrity and biocompatibility are state-of-the-art.

For example, a reed-switch can be operated by applying an external magnetic field. The disadvantages of the integration of reed-switches into such medical devices are related to the fact that when miniaturized, a reed-switch is configured as normally-open; therefore, to activate such a medical device using an internal reed-switch, it is either required to constantly maintain the presence of a magnetic field to keep the reed-switch in an ON-state, or to add electronic circuitry which senses the ON-state of the reed-switch as a control signal and activated the internal circuitry; this electronics requires stand-by current during storage.

Another examples of activation principles include the use of induction of current into integrated coils or antennas. This requires an additional specialized device to generate an appropriate electrical field to effectuate the energy transfer to the medical device. This further complicates the application for the user and also requires an electronics to sense the activation signal; this activation signal in turn requires stand-by current.

A further disadvantage of using state-of-the-art methods mentioned above is that reed-switches as well as the coils/antennas must have a certain size in order to be responsive to the external fields. Therefore, the miniaturization potential of the medical device is limited by the size of the components required in these methods.

The medical capsule must be activated shortly before the patient swallows it, since the electrical circuit in the medical capsule is only supplied by an integrated power source. Thus, the energy supply is only available to a limited extent. In addition to that, for better hygiene, it is preferred that the patient takes the capsule out of its package himself before swallowing it.

EP 0 460 327 A1 discloses a medical capsule having an outer cylinder and a piston movable in the outer cylinder, the piston being activated by an externally given signal so as to discharge a medicine to the outside of the capsule or to suck in a humor for a sampling purpose. The capsule has a remote controllable means including a normally-opened lead switch which connects a power supply to an activating means in response to an externally given magnetic signal thereby initiating activation of the medical capsule.

CN 106 823 113 A1 discloses a medical capsule device according to the present invention that can be applied safely and reliably in the gastrointestinal tract of a human or animal to release an agent in a predetermined position and that can be easily actuated and provides a large pore area in its actuated state; it may receive radio frequency signals by a radio frequency signal activation, regardless of the orientation of the device within the gastrointestinal tract.

U.S. Pat. No. 5,217,449 A1 discloses a medical capsule having an outer cylinder and a piston movable in the outer cylinder, the piston being activated by an externally given signal so as to discharge a medicine to the outside of the capsule or to suck a humor for a sampling purpose, as well as an apparatus for activating this medical capsule. The capsule has a remote-controllable means including a normally-opened lead switch which connects a power supply to an activating means in response to an externally given magnetic signal thereby initiating activation of the medical capsule, whereby a simple medical capsule which is operative with minimized electrical power consumption without affecting the living body can be obtained. The activating apparatus has a pair of magnetic field generating units arranged side-by-side so as to generate magnetic lines of force in various directions and to form magnetic fields covering a large area, thus ensuring correct activation of the medical capsule inside the living body.

The disadvantages of the known state of the art is that the medical capsule already consumes standby power which is required to detect/receive a signal to activate the medical capsule. This limits the shelf life of such devices, since the remaining power stored in the internal power storage must be sufficient to conduct the intended purpose of the device. Such devices run the risk of having insufficient power left due to power drain during excessive storage duration.

It is an object of the invention to improve or at least reduce the disadvantages and problems from the state of the art. It is particular object of the invention to provide a fast and easy way for the user to activate a medical capsule, provide a solution that has a high potential for miniaturization by using highly miniaturizable components and to eliminate the standby power.

This object is achieved by a medical capsule comprising the features of claim 1. Alternatively, dependent claim 2 can be used as independent claim instead of claim 1. Advantageous further developments of the invention are the subject matter of dependent claims.

BRIEF DESCRIPTION OF THE INVENTION

The core of the present invention is a medical capsule including an electrical circuit and an internal power source for selectively supplying the electrical circuit with electrical energy, wherein at least a photosensitive element is provided for initiating a supply of electrical energy to the electrical circuit when a light signal having a predetermined intensity is irradiated. In other words, the medical capsule is activated only when the photosensitive element is exposed to the predetermined light signal. The activation of the medical capsule is effected by supplying the electrical circuit with energy from the internal energy source. Alternatively, it is also conceivable that instead of the light intensity, the activation is dependent on a predetermined wavelength.

That means, the above-mentioned object of the invention is solved by an activation circuit in a medical capsule with integrated power source and a photosensitive element. The photosensitive element makes it possible that an activation signal, in this case a light signal, is received through the package of the medical capsule. Thus, the user, a short time before swallowing by the patient, can activate the medical capsule. It is preferred, that the patient can open the package of the capsule by himself. This has the advantage that no one other than the patient swallowing the medical capsule touches the unwrapped medical capsule.

This prevents the absence of bacteria or other contamination form anything other than the patient on the medical capsule. This also means that the patient is not disgusted to swallow the medical capsule if he takes it out of the package even before swallowing.

It is preferred, when a circuit arrangement comprising the internal power source, the photosensitive element, a switch driver, a switching element and the electrical circuit is provided. The power source has a positive supply conductor and a negative supply conductor, which are adapted to provide a positive supply voltage from a positive terminal and a negative supply voltage from a negative terminal. The at least one photosensitive element is adapted and provided to output a driver control signal to the switch driver, when the at least one photosensitive element is exposed to the light signal. The switch driver is adapted and provided to output a switch control signal to the switching element, if a driver control signal from the at least one photosensitive element and/or a feedback control signal is present. The switching element is adapted and provided to switch into an ON-state when the switch control signal is applied, and the electrical circuit is adapted and provided to return the feedback control signal to the switch driver.

It has to be noted, that the photosensitive element includes a photosensitive part, which receives the predetermined irradiating light. Hereinafter, only the photosensitive element will be mentioned wherein the photosensitive part is included to receive the activation signal.

In other words, the photosensitive element is designed to output a driver control signal while a photosensitive part of the photosensitive element is exposed to light. The driver is designed to control a switch when a driver control signal and/or if a feedback control signal is present. The switching element switches the positive supply voltage when a switch control signal is present. Alternatively, also the ground/negative supply voltage can be switched, or both. When the switch is in an ON-state, the electrical circuitry is powered. Then, the electrical circuitry may output a feedback control signal, with which the switch driver is signalled to maintain the ON-state of the switch even if the photosensitive element is not exposed to light and does not output a driver control signal.

That means, that an activation circuit is proposed that contains at least one photosensitive element, one switch driver and one switching element. For activation, a light source is given on a photosensitive part of the photosensitive element.

Further, it is advantageous, when the photosensitive element is connected between the positive supply conductor and the negative supply conductor of the internal energy supply, and is designed and provided to only have a current consumption when it is exposed to external light. In other words, the photosensitive element is designed in a way that essentially no current is consumed if it is not exposed to light, for example while the medical capsule is in a package.

It is preferred to connect the switch driver downstream of the photosensitive element and between the positive supply conductor and the negative supply conductor, and that it is designed and provided in a way that it only has a current consumption when the driver control signal and/or the feedback control signal is present. In other words, the switch driver is designed in a way that it essentially does not consume any current when no driver control signal and/or the feedback control signal is present.

Advantageously, the switching element is connected downstream of the switch driver in the positive supply conductor and/or in the negative supply conductor and only has a current consumption when the switch control signal is present. In other words, the switching element is designed in a way that essentially no current is flowing when no switch control signal is present.

Preferably, the switching element, when switching into the ON-state, is adapted and provided to apply a positively switched supply voltage to the electrical circuit. Alternatively, the switching element, when switching to the ON-state, is adapted and provided to apply a negative switched supply voltage to the electrical circuit, or both.

It is preferred, that the electrical circuit, by outputting the feedback control signal, signals the switch driver to maintain the ON-state of the switching element even when the light on the photosensitive element is off.

Further, it is preferred, that the switch driver has a feedback interface, which is adapted and provided to receive the feedback control signal of the electrical circuit.

Preferably, the photosensitive element is a series circuit consisting of a light-sensitive diode and a resistor, and the switch driver and the switching element are each formed by at least one MOSFET. In a preferred embodiment, the switch driver includes a n-MOSFET and the switching element includes a p-MOSFET.

In a preferred embodiment, the photosensitive part of the photosensitive element is a discrete semiconductor component such as a photosensitive diode. This includes various types of photosensitive semiconductor components such as a photodiode, a phototransistor or a light emitting diode (LED). An LED may exhibit behaviour comparable to a photosensitive element, as it allows a current flow when exposed to light. The advantage of using a photosensitive semiconductor component is, that it does essentially not permit a current flow when not exposed to any light even though an electrical voltage is applied. Therefore, a photosensitive semiconductor element can remain connected to the internal power source and therefore connected to the electrical voltage of the internal power source and at the same time does essentially not consume any power provided that it is not exposed to external light. During storage of this medical device, the medical device is stored in at least one non-transparent package, which is opened only when the device is about to be used. Therefore, the photosensitive element does no consume any power from the internal power source during storage of the device. In this preferred embodiment, the photosensitive element further contains at least one resistor, which forms a series connection with the photosensitive part between the positive supply conductor and negative supply conductor of the internal power source. In this way, a current flow between the positive supply conductor and negative supply conductor of the internal power source and through the photosensitive part when exposed to light must also flow through the resistor. This current flow through the resistor effectuates a electrical voltage according to Ohms law. This electrical voltage serves as driver signal being the output of the photosensitive element to the switch driver.

In a preferred embodiment, the switch driver contains a semiconductor component, preferably a field effect transistor (FET) such as a MOSFET. A FET is designed to provide a conductive path for an electrical current between its drain and source terminals when an electrical field generated by an electrical voltage at its gate terminal is provided. When no such electrical field is present, the path between the drain and source terminals is essentially non-conductive. Therefore, when this component is connected to a positive supply conductor and a negative supply conductor of a power source, essentially no current is flowing between the positive supply conductor and the negative supply conductor when no electrical field is present, while a current flow is permitted when an electrical field is present. In this preferred embodiment, the FET is connected to both the positive supply conductor and the negative supply conductor via resistors in series, which are designed to limit the current flow when an electrical field is applied, and to produce a switch control signal that is appropriate to control the switch.

In a preferred embodiment, the switch contains a semiconductor component, preferably a FET such as a MOSFET. When an appropriate switch control signal is supplied, the FET component in in its ON-state and provides a path for current flow and therefore for powering the electrical circuit of the device. If the switch control signal is absent, the FET is in its OFF-state and does essentially not permit any current flow to the electrical circuit of the device, and therefore avoids essentially any current consumption in its OFF-state.

In the preferred embodiment consisting of the preferred embodiments described above and illustrated in FIG. 2, the photosensitive element, the switch driver and the switch with its internal components are connected to the positive supply conductor and the negative supply conductor in a way that any current flow between the positive supply conductor and the negative supply conductor must go through a semiconductor element. This can be either a photosensitive part such as a photodiode, phototransistor or LED, or a field effect transistor (FET). These semiconductor components are designed and provided in a way that they are allowed to be in a state of non-conductivity when no active signal is present. Such active signal can be an exposure to external light, an electrical potential (voltage) or an electrical current.

Further, the present invention relates to a system comprising a medical capsule according to one of the above mentioned aspects in a package, and an extracorporeal device including a light source for emitting a light beam, wherein the package of the medical capsule is adapted and provided to be permeable to the predetermined luminous intensity. Alternatively, it is also conceivable that instead of the light intensity, the package is only permeable for a predetermined wavelength. Accordingly, the medical capsule is not activated by daylight and/or ambient light, but only by light of a certain luminous intensity. This luminous intensity value is selected in a way that it is not reached under normal circumstances such as in open daylight, in an office space, production room, clean room, doctor's office, hospital or the like, but it is reached in the very close proximity to light sources that emit light of a high luminous intensity from a small area such as LEDs or handheld flash lights, for example. Therefore, the medical capsule is not activated in normal daylight or ambient light, but only by light that is appropriately adjusted to a certain minimum predetermined light intensity and/or wavelength.

In other words, for activation, the corresponding extracorporeal device includes a light source, and the package of the medical capsule is shaped in a way that if the package is brought in touch with the extracorporeal device, the photosensitive element is activated.

In an preferred embodiment, the shape of the package is adapted to the shape of the extracorporeal device and the package is adapted and provided to position the extracorporeal device in exactly one predetermined position on the package. In other words, the position if the photosensitive element corresponds to a known position within the package of the medical capsule. The package has a shape/contour that corresponds to the shape/contour of the extracorporeal device in a way that it physically fits in a single position, corresponding to the position of best fit. The extracorporeal device comprises a light source, the position of which corresponds with the position of the photosensitive element of the medical capsule inside the package when the package is brought into contact with the extracorporeal device in the single position of best fit.

It is an advantage, when at least one guiding element is formed in the package and is adapted and provided to insert the extracorporeal device in the predetermined position of the package. In other words, for activation of the medical capsule, the user holds the package to the extracorporeal device at the position of best fit and activates the light source using the control button.

Preferably, the at least one guiding element is adapted and provided to guide a corner and a corresponding edge of the extracorporeal device and the medical capsule is arranged in the package so that, when the extracorporeal device is inserted, the position of the light source in the edge of the extracorporeal device coincides with the position of the photosensitive element of the medical capsule in the package.

Further, it is preferred that the package includes two guiding elements to define a guiding track. Finally, the extracorporeal device is inserted into the guiding track with its edge, where the light source is located. A second guiding element also serves as a stopper and thus determines the exact position of the extracorporeal device with respect to the medical capsule in the package. Therefore, the corner defines the relative position in all three axes.

Particularly, the medical capsule is activated by means of a control button on the extracorporeal device. This control button switches on the light source in order to activate the medical capsule via the photosensitive element. In other words, for activation, the corresponding extracorporeal device includes a light source, and the package of the medical capsule is shaped in a way that if the package is brought in touch with the extracorporeal device, and the light source is positioned in a way that its light path is in line with the photosensitive element of the medical capsule.

After switching on the light source with a control button, the electrical circuit is supplied with current and thus the medical capsule is activated. Therefore, the circuit configuration and therefore the medical capsule, does not consume energy from the internal power source until the circuit configuration has been activated. This solution allows a fast and easy way for the user to activate the medical capsule.

The control button of the extracorporeal device that activates the light source may be designed and provided as a hardware button integrated into the enclosure of the extracorporeal device or as a button on a touch screen that is incorporated into the extracorporeal device.

It should be expressly noted that the above aspects can solve the object of the invention individually or in any combination with each other and should therefore be claimable individually or in any combination within the scope of this application.

BRIEF DESCRIPTION OF FIGURES

Hereinafter, the invention will be described in detail by way of a preferred embodiment with reference to the accompanying figures, in which.

DESCRIPTION OF THE EMBODIMENTS

Figure 1:
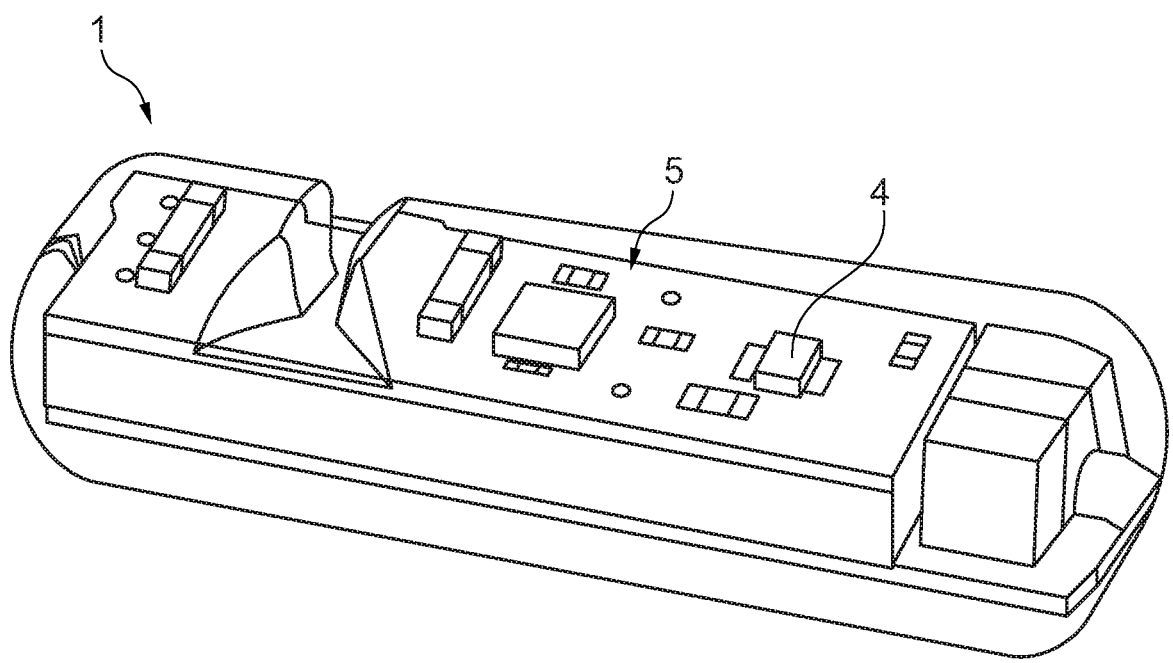
FIG. 1 schematically shows a medical capsule according to the invention.

FIG. 1 shows a medical capsule 1 according to the invention. A circuit configuration 5 is integrated in the medical capsule 1. The circuit configuration 5 comprises a photosensitive element 4 for activating the medical capsule 1. The medical capsule is supplied with electrical energy by an internal power source 3 (see FIG. 2). An electrical circuit 2 (see FIG. 2) is incorporated in the medical capsule 1, which has to be activated in order to be used in an intended medical procedure.

Figure 2:
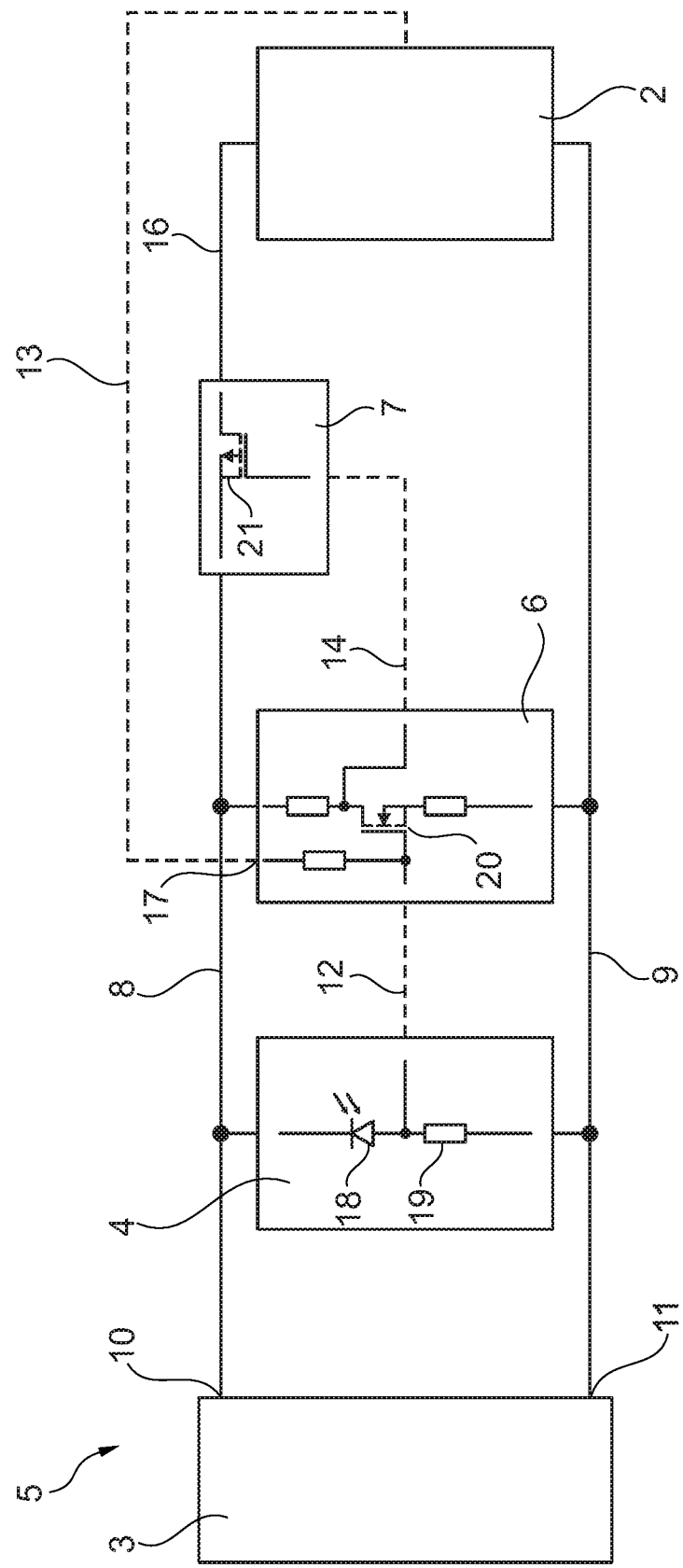
FIG. 2 shows a circuit configuration, which is incorporated in the medical capsule according to the invention.

FIG. 2 shows a circuit configuration 5, which is incorporated in the medical capsule 1 according to the invention. The circuit configuration 5 comprises the internal power source 3, the photosensitive element 4, a switch driver 6, a switching element 7 and the electrical circuit 2.

The power source 3 is preferably a battery. The power source 3 has a positive supply conductor 8 and a negative supply conductor 9. The positive supply conductor 8 is adapted to provide a positive supply voltage from a positive terminal 10. The positive terminal 10 is defined as one port/connector of the power source 3. The negative supply conductor 9 is adapted to provide a negative supply voltage from a negative terminal 11. The negative terminal 11 is defined as one other port/connector of the power source 3.

The photosensitive element 4 comprises a photosensitive part (not shown) and is adapted and provided to output a driver control signal 12 to the switch driver 6. The photosensitive element 4 is connected downstream of the power source 3. That means, the photosensitive element 4 is connected to the positive supply conductor 8 and to the negative supply conductor 9 and is parallel to the power source 3.

In the embodiment of FIG. 2, the photosensitive element 4 comprises a diode 18 as the photosensitive part, and a resistor 19 connected in series. The cathode of the diode 18 is connected to the positive supply conductor 8. The anode of the diode 18 is connected to one end of the resistor 19 and the other end of the resistor 19 is connected to the negative supply conductor 9.

The switch driver 6 is adapted and provided to output a switch control signal 14 to the switching element 7. The switch driver 6 is connected downstream of the power source 3 and the photosensitive element 4. That means, the switch driver 6 is connected to the positive supply conductor 8 and to the negative supply conductor 9 and is parallel to the power source 3 and to the photosensitive element 4.

In the embodiment of FIG. 2, the switch driver 6 comprises a n-type MOSFET 20. The gate of the n-type MOSFET receives the driver control signal 12. If the driver control signal 12 is present, the switch driver 6 consumes electrical energy and is able to output the switch control signal 14. The drain of the n-type MOSFET 20 is connected to a resistor and then to the positive supply conductor 8. The source of the n-type MOSFET 20 is connected to an additional resistor and then to the negative supply conductor 9.

Additionally, the switch driver 6 has a feedback interface 17 comprising one more resistor. The feedback interface 17 is adapted and provided to receive a feedback control signal 13. The electrical circuit 2 to the feedback interface 17 of the switch driver 6 transmits the feedback control signal 13. The feedback interface 17 is connected to the gate of the n-type MOSFET 20.

The switching element 7 is adapted and provided to switch into an ON-state when the switch control signal 14 is applied. The switching element 7 is connected to the switch driver 6 and the electrical circuit 2 in series. In the embodiment of FIG. 2, the switching element 7 comprises a p-type MOSFET 21. The gate of the p-type MOSFET 21 receives the switch control signal 14. If the switch control signal is present, the switching element 7 consumes electrical energy and is able to switch into the ON-state. Switching into the ON-state means supplying the electrical circuit 2 with switched positive supply voltage 16.

The electrical circuit 2 is adapted and provided to return the feedback control signal 13 to the feedback interface 17 of the switch driver 6. That means that when the switching element 7 is in an ON-state, the electrical circuit 2 is powered. The electrical circuit 2 may output a feedback control signal 13 with which the switch driver 6 is signalled to maintain the ON-state of the switching element 7 even if the photosensitive element 4 is not exposed to light and does not output a driver control signal 12. In summary, it can be said that once the electrical circuit 2 is activated, it remains on until the internal power source 3 is empty or the electrical circuit 2 discontinues the feedback control signal 13.

Figure 3:
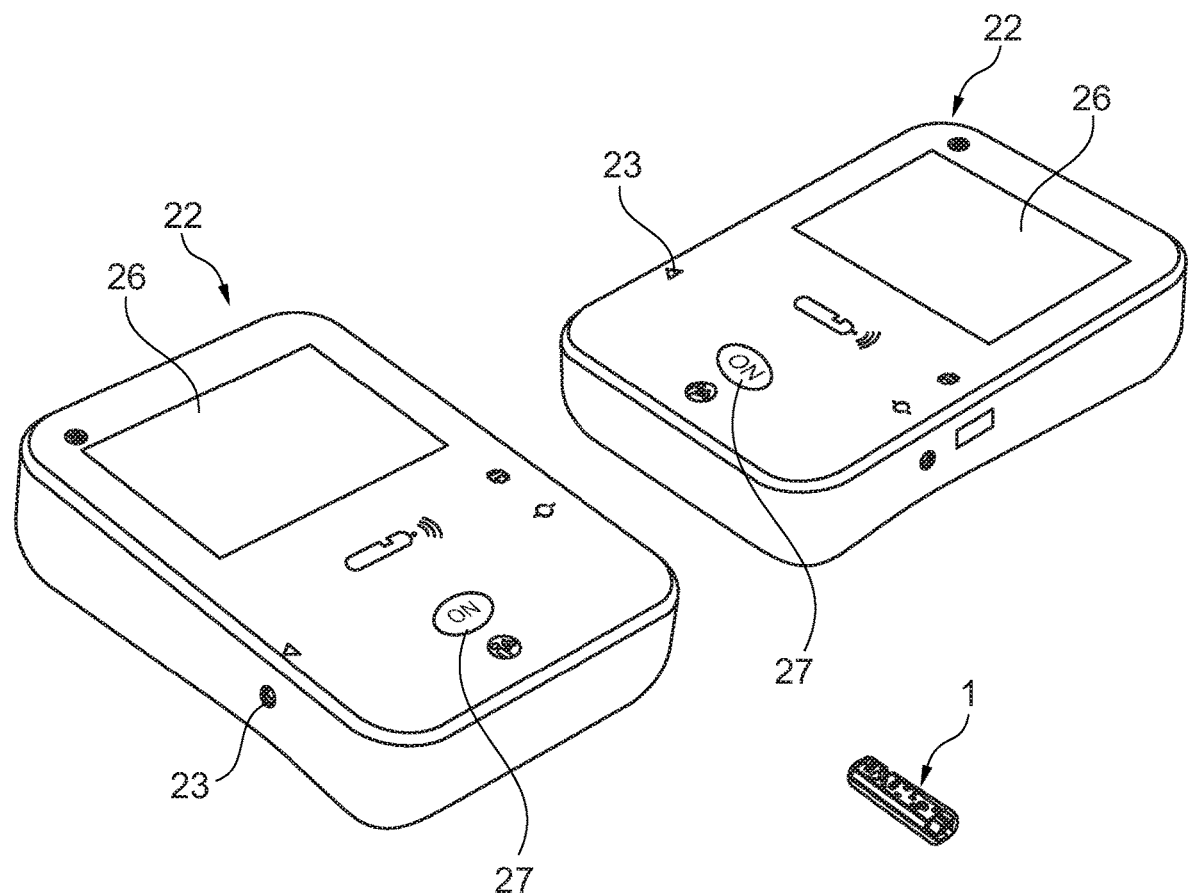
FIG. 3 shows an extracorporeal device and the medical capsule as well as the approximate size ratio to each other according to the invention.

FIG. 3 shows an extracorporeal device 22 and the medical capsule 1 as well as the approximate size ratio to each other according to the invention. The extracorporeal device 22 is a device such as a mobile phone or another device, which is able to transmit and receive data information. The extracorporeal device 22 comprises a light source 23, which is used to output a light signal to the photosensitive element 4, and a display 26. In the embodiment of FIG. 3, the light source 23 is integrated in an edge of the extracorporeal device 22. A control button 25, preferably as a touch button, is integrated in the display 26 (see FIG. 4). In addition, the extracorporeal device 22 comprises an ON-button 27 to switch the extracorporeal device 22 on.

Figure 4:
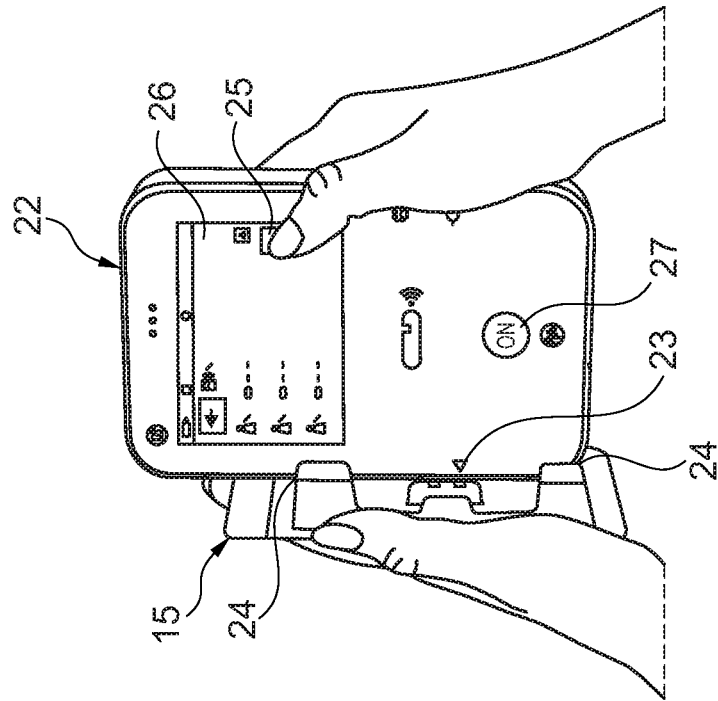
FIG. 4 shows the system comprising the medical capsule in a package and the extracorporeal device according to the invention.
Figure 4:
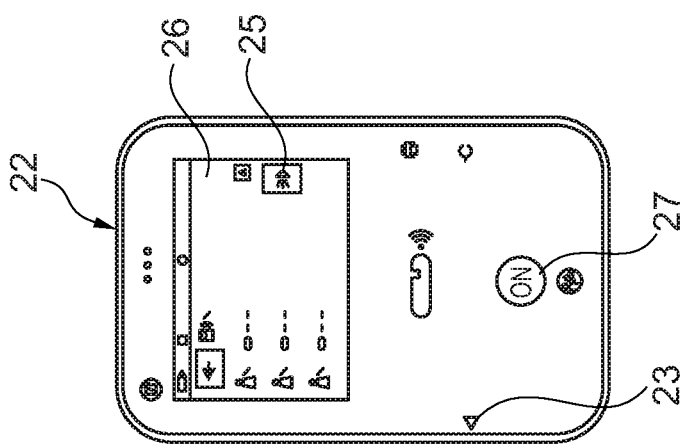
Figure 4:
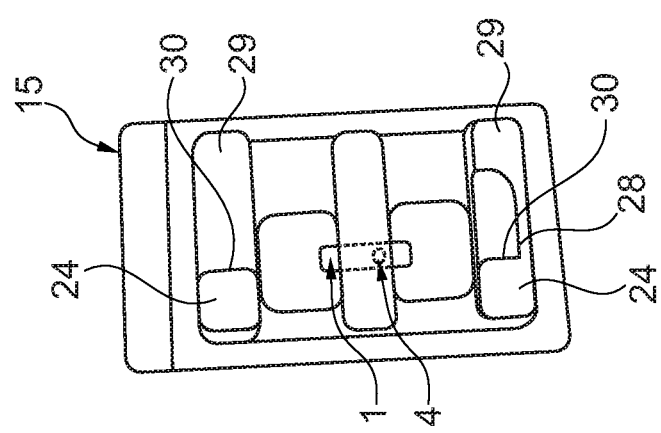

FIG. 4 shows the system comprising the medical capsule 1 in a package 15 and the extracorporeal device 22 according to the invention. On the left side of FIG. 4, the package 15 with the medical capsule 1 is shown separately from the extracorporeal device 22. On the right side of FIG. 4, the package 15 with the medical capsule 1 with the extracorporeal device 22 inserted is shown.

The package 15 has a shape/contour that corresponds to the shape/contour of the extracorporeal device 22. The surface of the package 15 of the medical capsule 1 is adapted and provided to be permeable for the predetermined intensity. Alternatively, it is also conceivable that instead of the light intensity, the package 15 is only permeable for a predetermined wavelength. Accordingly, the medical capsule 1 is not activated by daylight and/or ambient light, but only by light, preferably appropriately adjusted by the package 15, which reaches the predetermined light intensity. The light source 23 is adapted and provided to penetrate the package 15 with its light intensity in order to hit the photosensitive element 4 of the medical capsule 1 and activate it.

The package 15 comprises at least one guiding element 24. The at least one guiding element 24 is adapted and provided to guide an edge of the extracorporeal device 22. Preferably, the at least one guiding element 24 forms a guiding track. The guiding track is built by the two guiding element 24. In addition, the second guiding element 24 is adapted and provided to serve as a stopper 28. Preferably, the second guiding element 24 is provided in the lower part if the package 15. Therefore, the second guiding element 24 is designed to stop the inserted extracorporeal device 22 at the predetermined position.

The guiding elements 24 are designed as incline elevations 28 on the package 15. Accordingly, there is a flat inclined section which serves to insert the extracorporeal device 22 smoothly. It is preferable to place the flat inclined section on the right half of the package 15, provided that the light source 23 is in the left edge of the extracorporeal device 22. On the left side of the package 15, the guiding elements 24 each have a steep elevated section 20, which forms an edge against which the edge of the extracorporeal device 22 is placed. This means that the edge of the extracorporeal device is in contact with the medical capsule 1 in the package 15. In other words, the medical capsule 1 is part of the guiding track.

The extracorporeal device 22 according to FIG. 3 shows the display 26 and the control button 25 in the display 26 for activating the light source 23.

Therefore, the shape of the package 15 is adapted to the shape of the extracorporeal device 22 and the package 15 is adapted and provided to position the extracorporeal device 22 in exactly one predetermined position on the package 15 according to the right side of FIG. 5. The at least one guiding element 24 is adapted and provided to guide the edge of the extracorporeal device 22, and the medical capsule 1 is arranged in the package 15 so that, when the extracorporeal device 22 is inserted, the position of the light source 23 in the edge of the extracorporeal device 22 coincides with the position of the photosensitive element 4 of the medical capsule 1 in the package 15.

In summary, the medical capsule 1 is adapted, by means of a control button 25 on a display 26 of the extracorporeal device 22, to switch on the light source 23 in order to activate the medical capsule 1 via the photosensitive element 4.

REFERENCE

1 Medical capsule
2 Electrical circuit
3 Power source
4 Photosensitive element
5 Circuit configuration
6 Switch driver
7 Switch element
8 Positive supply voltage
9 Negative supply voltage
10 Positive terminal
11 Negative terminal
12 Driver control signal
13 Feedback control signal
14 Switch control signal
15 Package
16 Switched positive supply voltage
17 Feedback interface
18 Diode
19 Resistor
20 n-type MOSFET
21 p-type MOSFET
22 Extracorporeal device
23 Light source
24 Guiding element
25 Control button
26 Display
27 ON-button
28 Stopper
29 Flat inclined section
30 Steep elevated section

The invention claimed is:
1. A medical capsule comprising:
an electrical circuit;
an internal power source for selectively supplying the electrical circuit with a supply of electrical energy; and
a power switch circuit comprising:
  a switching element;
  a switch driver connected to the electrical circuit by a switched power supply connection;
  at least one photosensitive element configured to, upon being irradiated by a light signal having a predetermined intensity, output a driver control signal to the switch driver to initiate the supply of electrical energy to the electrical circuit by the switched power supply connection, and a feedback control circuit comprising a communication path separate from the switched power supply connection, wherein the feedback control circuit is configured to convey a feedback control signal from the electrical circuit to the switch driver to maintain the supply of electrical energy to the electrical circuit when the feedback control signal is present, wherein the switch driver comprises at least one field effect transistor and a feedback interface configured to receive the feedback control signal of the electrical circuit, wherein the switch driver further comprises at least two resistors, and wherein a drain of the at least one field effect transistor is connected, via a first resistor of said at least two resistors, to a positive supply conductor of the internal power source and a source of the at least one field effect transistor is connected, via a second resistor of said at least two resistors, to a negative supply conductor of the internal power source.

2. The medical capsule according to claim 1, wherein:

the internal power source has the positive supply conductor and the negative supply conductor, which are adapted to provide a positive supply voltage from a positive terminal and a negative supply voltage from a negative terminal, respectively, and the at least one photosensitive element is adapted and provided to output the driver control signal to the switch driver, when:

(i) the at least one photosensitive element is exposed to the light signal, and/or (ii) the feedback control signal is present, the switch driver is adapted and provided to output a switch control signal to the switching element, and the switching element is adapted and provided to switch into an ON-state when the switch control signal is applied.

3. The medical capsule according to claim 2, wherein the at least one photosensitive element is connected between the positive supply conductor and the negative supply conductor, but only has a current consumption when (i) or (ii) occurs.

4. The medical capsule according to claim 2, wherein the switch driver is connected in parallel to the at least one photosensitive element and is connected between the positive supply conductor and the negative supply conductor, but only has a current consumption when the driver control signal is present.

5. The medical capsule according to claim 2, wherein the switching element is connected in series in the positive supply conductor or in the negative supply conductor between the switch driver and the electrical circuit, and the switching element only has a current consumption when the switch control signal is present.

6. The medical capsule according to claim 5, wherein the switching element, when switching to the ON-state, is adapted and provided to apply a switched positive supply voltage to the electrical circuit.

7. The medical capsule according to claim 5, wherein the switching element, when switching to the ON-state, is adapted and provided to apply a switched negative supply voltage to the electrical circuit.

8. The medical capsule according to claim 1, wherein the electrical circuit, by outputting the feedback control signal, signals the switch driver to maintain an ON-state of the switching element even when the light on the at least one photosensitive element is off.

9. The medical capsule according to claim 1, wherein the at least one photosensitive element is a series circuit consisting of a diode and a resistor, and the switch driver and the switching element are is formed by at least one field effect transistor.

10. A system comprising a medical capsule according to claim 1, in a package, and an extracorporeal device including a light source for emitting a light beam, wherein the package of the medical capsule is non-transparent and is adapted and provided to be permeable exclusively to the predetermined intensity of the light beam of the light source.

11. The system according to claim 10, wherein a shape of the package is adapted to a shape of the extracorporeal device and the package is adapted and provided to position the extracorporeal device in exactly one predetermined position on the package.

12. The system according to claim 10, wherein at least one guiding element is formed in the package and is adapted and provided to insert the extracorporeal device in the at least one predetermined position of the package.

13. The system according to claim 12, wherein the at least one guiding element is adapted and provided to guide an edge of the extracorporeal device, and the medical capsule is arranged in the package so that, when the extracorporeal device is inserted, a position of the light source in the edge of the extracorporeal device coincides with a position of the at least one photosensitive element of the medical capsule in the package.

14. The system according to claim 10, wherein the medical capsule is adapted, by means of a control button on a display of the extracorporeal device, to switch on the light source in order to activate the medical capsule via the at least one photosensitive element.

15. The medical capsule according to claim 1, wherein the feedback interface is connected to a gate of the at least one field effect transistor.

16. The medical capsule according to claim 1, wherein the feedback interface comprises a third resistor.

* * * * *

UNITED STATES PATENT AND TRADEMARK OFFICE
CERTIFICATE OF CORRECTION

| | | |
|---|---|---|
| PATENT NO. | : 12,171,580 B2 | Page 1 of 1 |
| APPLICATION NO. | : 17/160937 | |
| DATED | : December 24, 2024 | |
| INVENTOR(S) | : Schostek et al. | |

It is certified that error appears in the above-identified patent and that said Letters Patent is hereby corrected as shown below:

On the Title Page

Item (72) Inventors: Sebastian Schostek, delete "Tübingen" and insert --Mössingen--; Gunnar Anhöck, delete "Tübingen" and insert --Reutlingen--; and In the Claims In Column 12, Claim 9, Lines 19-20, delete "and the switch driver and the switching element are is" and insert --and the switching element is--.

Signed and Sealed this
First Day of April, 2025

Coke Morgan Stewart
*Acting Director of the United States Patent and Trademark Office*